US00PP24007P2

(12) United States Plant Patent
Kitahara

(10) Patent No.: US PP24,007 P2
(45) Date of Patent: Oct. 29, 2013

(54) ***PHLOX* PLANT NAMED 'PPPHL07101'**

(50) Latin Name: *Phlox subulata×stolonifera*
Varietal Denomination: PPPHL07101

(75) Inventor: Akiko Kitahara, Mizuho (JP)

(73) Assignee: Amerinova Properties LLC, Bonsall, CA (US)

( * ) Notice: Subject to any disclaimer, the term of this patent is extended or adjusted under 35 U.S.C. 154(b) by 54 days.

(21) Appl. No.: 13/385,656

(22) Filed: Feb. 28, 2012

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Kent L Bell
(74) *Attorney, Agent, or Firm* — Cassandra Bright

(57) ABSTRACT

A new and distinct *Phlox* cultivar named 'PPPHL07101' is disclosed, characterized by vigorous plant growth and early flowering, with blooms produced over a long period of time. Plants have a good resistance to powdery mildew and produce rose pink flowers. The new variety is a *Phlox*, normally produced as an outdoor ornamental plant for containers or gardens.

1 Drawing Sheet

Latin name of the genus and species: *Phlox subulata× stolonifera.*

Variety denomination: 'PPPHL07101'.

BACKGROUND OF THE INVENTION

The new cultivar was discovered as a result of a planned breeding program directed by the inventor, Akiko Kitahara, a citizen of Japan. The seed parent is the unpatented variety of *Phlox subulata* 'Daniel Cushion' and the pollen parent is an unnamed, unpatented variety of *Phlox stolonifera*. The cross resulting in 'PPPHL07101' was made Apr. 18, 2006. The new variety was discovered Sep. 25, 2007, by the inventor in a non-commercial nursery in Higashiomi Shiga, Japan.

Asexual reproduction of the new cultivar 'PPPHL07101' by vegetative cuttings was first performed Sep. 25, 2007 at a non-commercial nursery in Higashiomi Shiga, Japan. Multiple generations have since been produced and have shown that the unique features of this cultivar are stable and reproduced true to type in successive generations. The new cultivar was first sold and made available to the public in April 2011.

SUMMARY OF THE INVENTION

The cultivar 'PPPHL07101' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PPPHL07101' These characteristics in combination distinguish 'PPPHL07101' as a new and distinct *Phlox* cultivar:

1. Vigorous growth habit, compared to existing *Phlox subulata* varieties known to the Inventor.
2. Early flowering.
3. Long flowering period.
4. Good resistance to powdery mildew.
5. Rose pink colored flowers.

PARENT COMPARISON

Plants of the new cultivar 'PPPHL07101' are similar to plants of the seed parent, *Phlox subulata,* 'Daniel Cushion', in most horticultural characteristics, however, plants of the new cultivar 'PPPHL07101' produce flowers over a significantly longer period than the seed parent. Flower color of the new variety is a lighter and different shade of pink. Additionally, plants of the new variety are much more vigorous and produce larger flowers than the seed parent.

Plants of the new cultivar 'PPPHL07101' are similar to plants of the pollen parent, an unnamed plant of *Phlox stolonifera* in most horticultural characteristics, however, plants of the new cultivar 'PPPHL07101' produce flowers over a significantly longer period than the pollen parent. Flower color of the new variety is a different shade of pink. Additionally, the new variety has smaller foliage than the pollen parent.

COMMERCIAL COMPARISON

'PPPHL07101' can be compared to the commercial variety *Phlox subulata* 'Drummonds Pink', unpatented. The two varieties are very similar in most horticultural characteristics, however, plants of 'PPPHL07101' produce longer peduncles than 'Drummonds Pink' and produce larger flowers of a different shade of pink. Additionally, plants of 'PPPHL07101' are more mounding in growth habit compared to the flat, mat forming habit of 'Drummonds Pink'.

'PPPHL07101' can be compared to the commercial variety *Phlox subulata* 'Fort Hill', unpatented. The two varieties are very similar in most horticultural characteristics, however, plants of 'PPPHL07101' produce longer peduncles, larger flowers and flowers of a different pink shade than 'Fort Hill'. Additionally, plants of 'PPHL07101' produce flowers over a longer period of time, from Spring through Summer, compared to the Spring only bloom of 'Emerald Blue'.

BRIEF DESCRIPTION OF THE PHOTOGRAPH

The accompanying photograph in FIG. 1 illustrates in full color a of typical plant of 'PPPHL07101' grown in a poly house, in Bonsall, Calif., in a commercial 6 inch container. Age of the plant photographed is approximately 10 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'PPPHL07101' plants grown in a poly house, in Bonsall, Calif., in a commercial 6 inch container. The growing temperature ranged from 60° F. to 75° F. daytime and 50° F. to 60° F. at night. No chemical treatments were given. Measurements and numerical values represent averages of typical plant types.

Botanical classification: *Phlox subulata×stolonifera* 'PPPHL07101'.

PROPAGATION

Time to initiate roots during summer: Approximately 6 days at temperatures between 17° C. and 29° C.

Time to initiate roots during winter: Approximately 5 days at temperatures between 17° C. and 21° C.

Time to produce a rooted cutting: 30 to 35 days.

Root description: Fine, fibrous, moderately dense rooting habit.

PLANT

Pot size of plant described: 6 inch diameter pot.

Age of plant described: Approximately 10 Weeks.

Growth habit: Mounding, spreading.

Height:

- *To top of flowers*.—Approximately 10 cm.
- *To top of foliage plane*.—Approximately 16 cm.

Plant spread: Approximately 21 cm.

Growth rate: Rapid.

Branching characteristics: Very well branched.

Length of primary lateral branches: Approximately 6 cm.

Quantity of primary lateral branches: More than 20 per plant.

Characteristics of primary lateral branches:

- *Form*.—Round.
- *Diameter*.—Approximately 0.2 cm.
- *Color*.—Near RHS Green 143C, new growth near Red-Purple 59C.
- *Texture*.—Densely pubescent. Hairs minute, less than 0.1 cm.
- *Strength*.—Flexible, moderately strong.

Internode length: Average 0.5 to 1.0 cm.

FOLIAGE

Leaf:

- *Arrangement*.—Opposite.
- *Quantity*.—Approximately 10 per branch.
- *Average length*.—Approximately 2.8 cm.
- *Average width*.—Approximately 0.8 cm.
- *Shape of blade*.—Linear.
- *Apex*.—Acute.
- *Base*.—Blunt.
- *Margin*.—Entire.
- *Texture of top surface*.—Pubescent.
- *Texture of bottom surface*.—Pubescent.
- *Aspect*.—Very slightly recurved to flat.
- *Color*.—Young foliage upper side: Near RHS Green 137B, 143B at base. Young foliage under side: Near RHS Green 143C, tip 137B. Mature foliage upper side: Near RHS Green 139A. Mature foliage under side: Near RHS Green 137B.
- *Venation*.—Type: Pinnate. Venation color upper side: Near RHS Yellow-Green 144C. Venation color under side: Near RHS Yellow-Green 144C.
- *Petiole*.—Sessile, petiole not present.

FLOWER

Natural flowering season: Spring through Summer.

Inflorescence and flower type and habit: Clustered cymes of salverform flowers. 2 to 5 cymes, of 3 to 5 flowers.

Rate of flower opening: 3 to 5 days from bud to fully opened flower.

Flower longevity on plant: Approximately 7 to 10 days.

Approximate quantity of flowers per plant: Approximately 30.

Persistent or self-cleaning: Persistent.

Inflorescence:

- *Depth*.—Approximately 6 cm.
- *Width*.—Approximately 9 cm.

Individual cyme:

- *Depth*.—Approximately 5.0 cm.
- *Width*.—Approximately 3.0 cm.

Bud:

- *Shape*.—Cylindric.
- *Length*.—Approximately 2.0 cm.
- *Diameter*.—Approximately 0.4 cm.
- *Color*.—Near RHS Red-Purple 72B.

Flower size:

- *Length*.—Approximately 2.5 cm.
- *Diameter*.—Approximately 2.1 cm.
- *Flower tube length*.—Approximately 1.6 cm.
- *Flower tube diameter at basal end*.—Approximately 0.3 cm.
- *Flower tube diameter at distal end*.—Approximately 0.4 cm.

Petals:

- *Length from throat*.—Approximately 1.4 cm.
- *Width*.—Approximately 1.1 cm.
- *Quantity*.—5.
- *Texture*.—Glabrous.
- *Apex*.—Irregular obtuse shallow lobes, 2 to 6.
- *Margin*.—Entire.

Color:

- *When opening*.—Upper surface: Near RHS Red-Purple 71C. Lower surface: Near RHS Red-Purple 71C.
- *Fully opened*.—Upper surface: Near RHS Red-Purple 64C. Lower surface: Near RHS Red-Purple 70 B. Flower throat (inside): Near RHS Purple 76D, flushed faintly 75B. Flower throat, visible rim: Near RHS Purple 75B. Flower tube (outside): Near RHS Purple 76D, flushed faintly 75B.
- *Fading*.—Upper surface: Near RHS Red-Purple 72B, apex Violet N87C. Lower Surface: Near RHS Purple N78C.

Calyx/sepals:

*Quantity per flower.*—5.

*Shape.*—50% fused together, linear shape.

*Length.*—Approximately 0.7 cm.

*Width.*—Approximately 0.2 cm.

*Apex.*—Acute.

*Base.*—Fused.

*Margin.*—Entire.

*Texture.*—Pubescent.

*Color.*—Upper Surface: Near RHS Green 137A near apex, base near 143C. Lower Surface: Near RHS Green 137A near apex, base near 143C.

Peduncle:

*Length.*—Average 4.1 cm.

*Diameter.*—Average 0.2 cm.

*Color.*—Near RHS Green 143C.

*Texture.*—Pubescent. Orientation: Approximately 25° angle from stem, undulating.

Pedicel:

*Length.*—Approximately 0.7 cm.

*Diameter.*—Approximately 0.1 cm.

*Color.*—Near RHS Green 143C.

*Texture.*—Pubescent. Orientation: Approximately 15° angle from peduncle, undulating.

Fragrance: Musty to faintly sweet.

REPRODUCTIVE ORGANS

Stamens:

*Number.*—5.

*Filament length.*—Fused to petals, unfused portion 0.1 cm.

Anthers:

*Length.*—0.1 cm.

*Shape.*—Linear.

*Color.*—Near RHS Yellow 13A.

*Pollen.*—Color: Near Yellow-Orange 21A. Quantity: Moderate.

Pistil:

*Number.*—1.

*Length.*—1.8 cm.

*Style.*—Length: 1.4 cm.

*Color.*—Near RHS White N155C.

*Stigma.*—Shape: 3 branched. Color: Near RHS Greyed-Purple 187B. Ovary Color: Near RHS Green 143A.

OTHER CHARACTERISTICS

Seeds and fruits: Not observed to date.

Disease/pest resistance: Resistance to powdery mildew has been observed.

Temperature tolerance: Tolerant to least −1° C. without damage. Upper temperature tolerance to at least 30° C.

What is claimed is:

1. A new and distinct cultivar of *Phlox* plant named 'PPPHL07101' as herein illustrated and described.

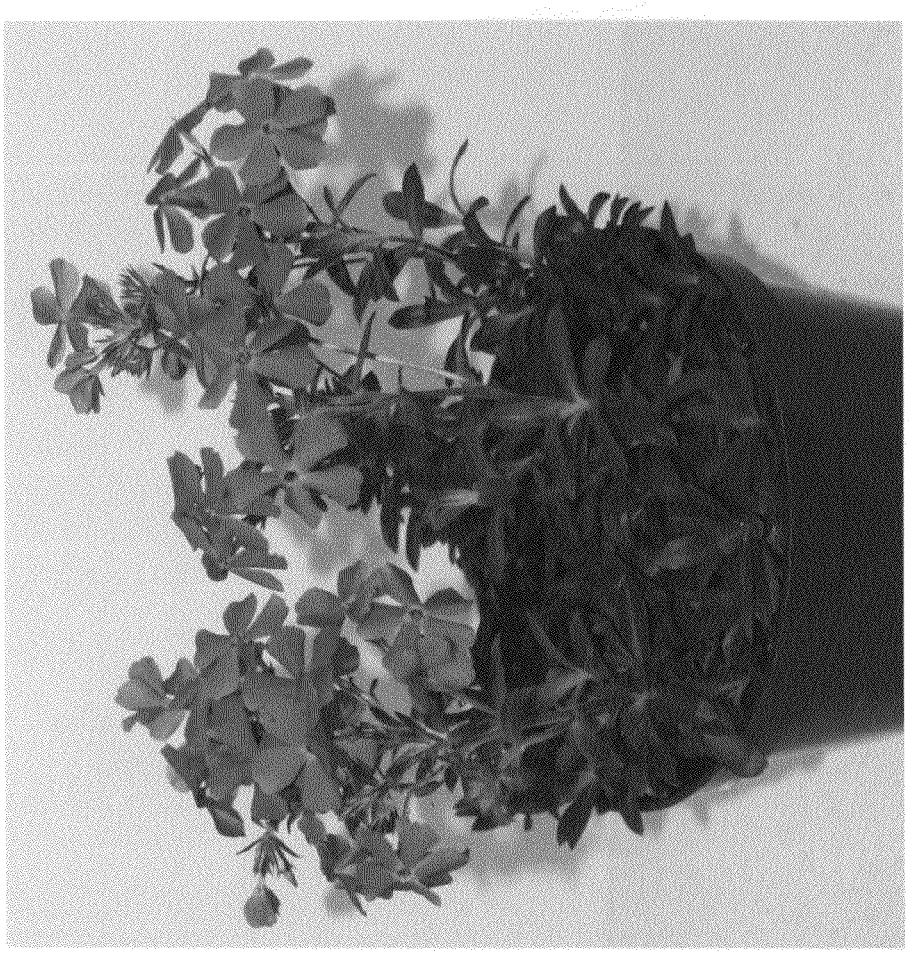

* * * * *